(12) United States Patent
Mehta

(10) Patent No.: US 9,623,170 B2
(45) Date of Patent: *Apr. 18, 2017

(54) LAVAGE DEVICE

(71) Applicant: Ketan C. Mehta, Santa Rosa, CA (US)

(72) Inventor: Ketan C. Mehta, Santa Rosa, CA (US)

( * ) Notice: Subject to any disclaimer, the term of this patent is extended or adjusted under 35 U.S.C. 154(b) by 213 days.

This patent is subject to a terminal disclaimer.

(21) Appl. No.: 14/500,844

(22) Filed: Sep. 29, 2014

(65) Prior Publication Data

US 2015/0105738 A1    Apr. 16, 2015

Related U.S. Application Data

(63) Continuation of application No. 11/753,556, filed on May 24, 2007, now Pat. No. 8,845,598.

(51) Int. Cl.
*A61M 3/02* (2006.01)

(52) U.S. Cl.
CPC ........ *A61M 3/0241* (2013.01); *A61M 3/0245* (2013.01); *A61M 2210/0618* (2013.01)

(58) Field of Classification Search
CPC .............. A61M 3/0241; A61M 3/0245; A61M 2210/0618

See application file for complete search history.

(56) References Cited

U.S. PATENT DOCUMENTS

| | | |
|---|---|---|
| 2,309,834 A | 2/1943 | Englund |
| 3,625,389 A | 12/1971 | Bartlow |
| 5,031,517 A | 7/1991 | Yeh |
| 5,779,102 A | 7/1998 | Smith |
| 5,806,723 A | 9/1998 | DuBose |
| 6,241,705 B1 | 6/2001 | Ko-Wen |
| 6,520,384 B2 | 2/2003 | Mehta |
| 6,669,059 B2 | 12/2003 | Mehta |
| 7,971,761 B1 | 7/2011 | Kudlu |
| 2003/0229306 A1 | 12/2003 | Sherman |
| 2008/0294124 A1 | 11/2008 | Mehta |

*Primary Examiner* — Bradley Osinski
(74) *Attorney, Agent, or Firm* — Fish & Richardson P.C.

(57) ABSTRACT

A device for holding fluid has a spout for pouring the fluid. The device includes a lid with an aperture. The aperture can be covered by a user's fingers or uncovered to control the flow of fluid out of the spout.

17 Claims, 5 Drawing Sheets

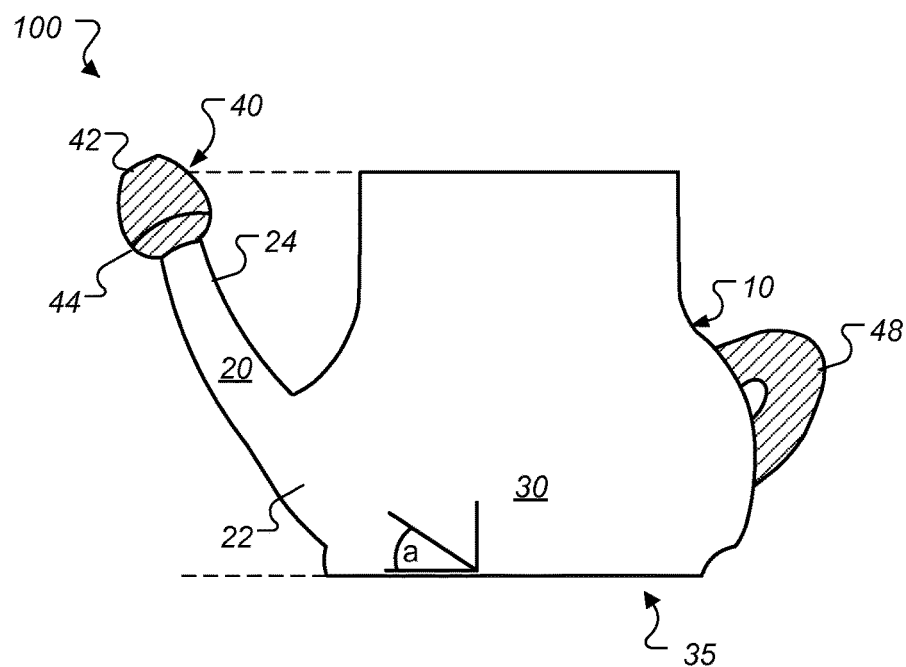
FIG._1
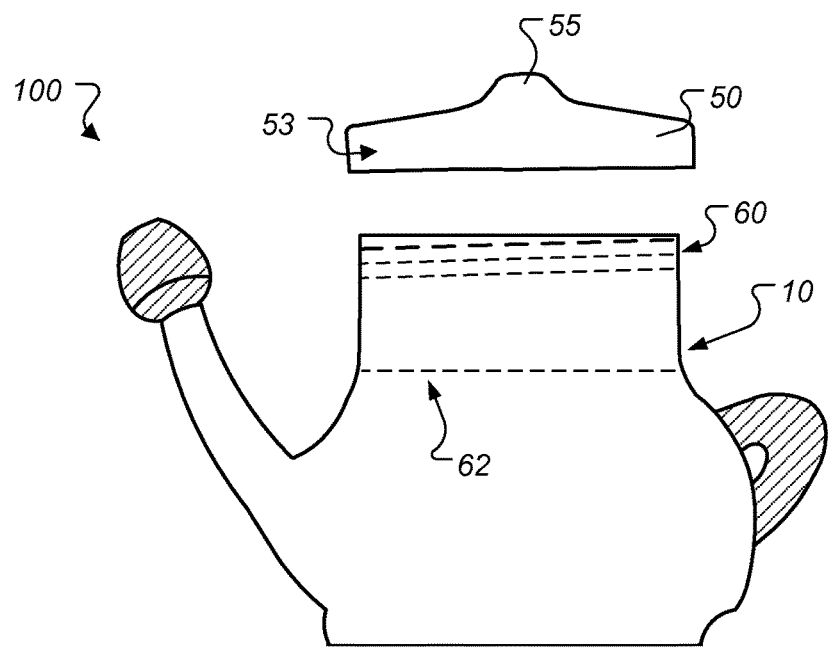
FIG._2

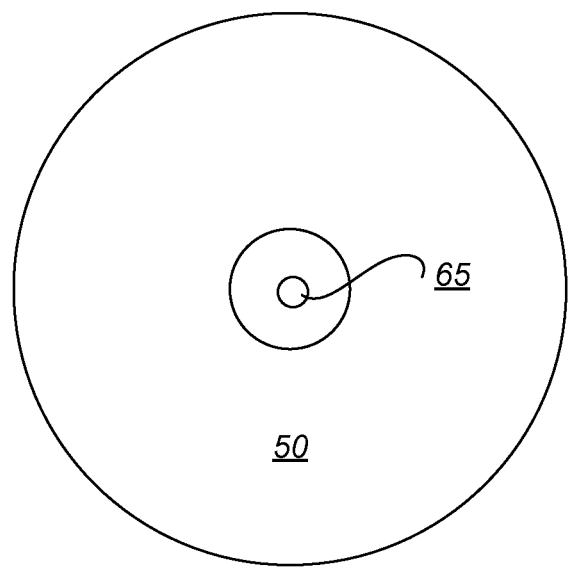
FIG._3A
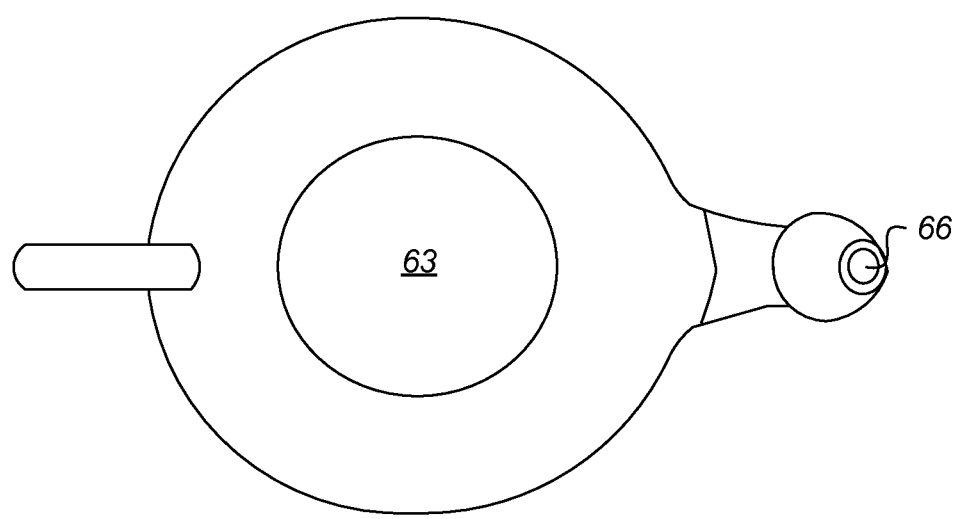
FIG._3B

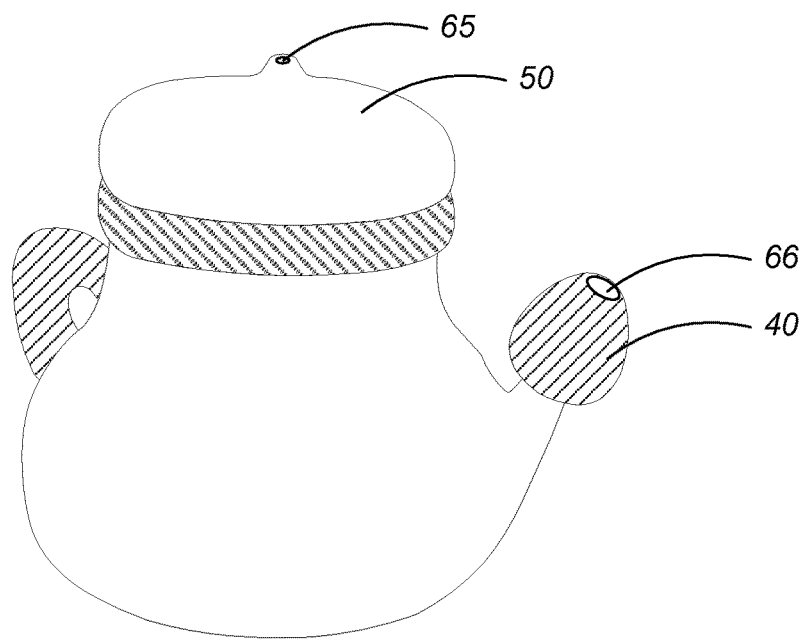
FIG._4
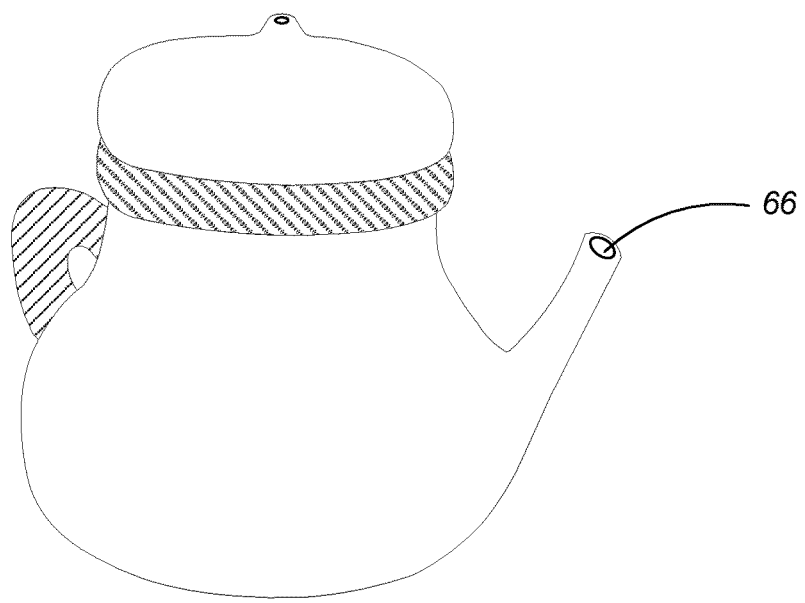
FIG._5

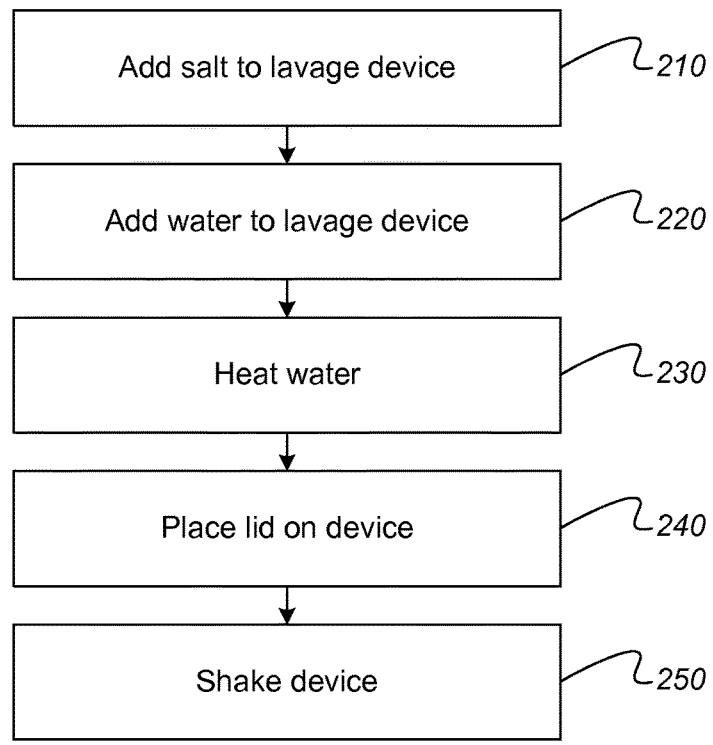
FIG._6
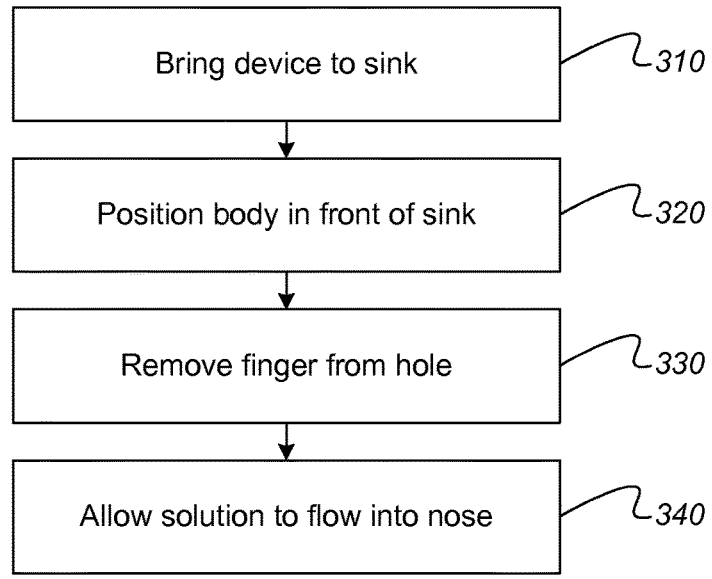
FIG._7

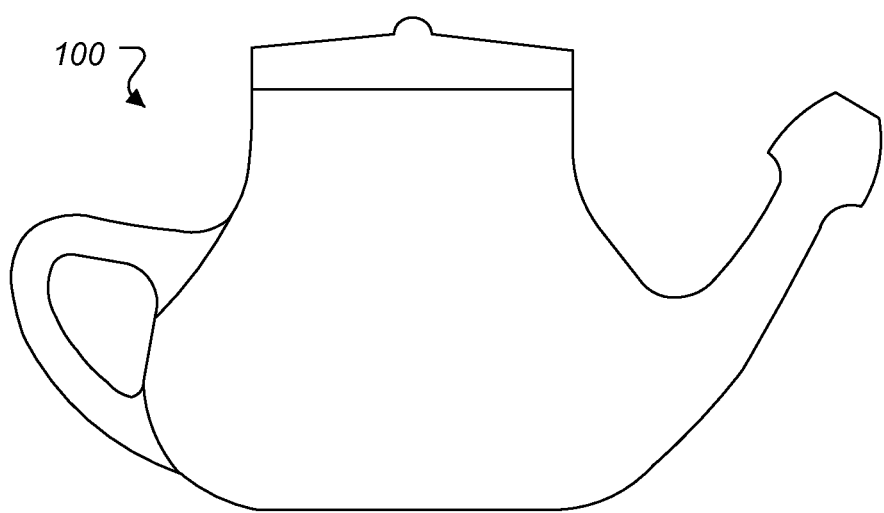
FIG._8

LAVAGE DEVICE

CROSS-REFERENCE TO RELATED APPLICATION

This application is a continuation of U.S. application Ser. No. 11/753,556, filed on May 24, 2007, the disclosure of which is hereby incorporated by reference in its entirety.

BACKGROUND

This invention relates to nasal lavage.

People in many parts of the world perform nasal cleansing using a neti pot on a routine basis, like brushing their teeth or showering. Nasal cleansing is even incorporated into some forms of yoga practice, such as in Jala neti. Jala neti is a Sanskrit term that refers to cleansing and means "water cleansing". Often, the solution for rinsing the nasal passages using a neti pot is a saline solution. Some people use nasal rinsing to reduce allergies, improve breathing, eliminate post-nasal drip or sinus infections, moisten dry nasal passages, avoid catching a cold or to generally improve one's health. Some people also claim that Jala neti improves one's vision by cleaning the tear ducts, improves the sense of smell and improves one's sense of taste.

Some problems with Jala neti can be that the solution flow from the neti pot can be difficult to control and using the neti pot can be somewhat messy.

SUMMARY

The device described herein is configured for ease of use, controllability of the solution exiting the device and comfort for the user.

In one aspect, a device is described that has a body surrounding a cavity; a tubular portion with an interior space fluidly connected to the cavity in the body where the tubular portion has an extended end opposite to the body; an end portion at the extended end of the tubular portion and a lid. The end portion has a lower region directly adjacent to the extended end and the diameter of the lower region is greater than the diameter of the extended end. The end portion tapers inwardly along a direction away from the tubular portion. A termination of the end portion has an aperture therethrough. The end portion has a curved surface leading from approximately the aperture to the lower region. The lid is configured to form a liquid tight seal with the body, the lid having an aperture therein.

Embodiments of the device can include one or more of the following features. The aperture in the end portion can have a diameter that is less than the diameter of the extended end. The device can include a handle on an opposite end of the body from the tubular portion. The tubular portion can taper down from a widest portion adjacent to the body to the extended end. The body can have a flattened portion configured to provide a stable resting surface for the body and the tubular portion can extend from the body at an angle between about 30° and 60° with a surface co-planar with the flattened portion. The body can have a bulbous portion that is fluidly connected to the interior space of the tubular portion. The body can include a line indicating a volume of liquid in the cavity. The lid can be detachably secured to the body. The body can have an opening that is covered by the lid. The opening can have a diameter of at least about 2 inches. The lid can have a cylindrical portion with a threaded inner diameter surface that is configured to mate with a cylindrical portion of the body having a threaded outer diameter surface. The end portion can be sized to fit snuggly against the interior of a human nostril. The end portion can be about 0.7 inches in length. The lower region of the end portion can have a width of about 0.8 inches and the termination has a width of about 0.4 inches. The lower region of the end portion can have a width greater than a width able to fit in an average sized human nostril. The end portion, tubular portion and body can be formed as a unitary piece. The body can be formed of plastic. The aperture in the end portion can be about 0.25 inches in diameter.

The devices described herein may include one or more of the following advantages. A device may have a portion that fits comfortably in a user's nostril, but is shaped to prevent the spout of the device from entering too far into the nose and causing injury. The spout can be at an angle to the body of the device that allows the user to pour the solution into a nostril without tilting his or her head significantly. The devices can have a sufficiently wide mouth that allows for easy pouring of liquids and salts into the device without risk of spilling. In some implementations, the device has a lid that protects the solution from contamination, such as from dust in the environment coming into contact with the solution. The lid also prevents solution from spilling out of the device. The lid can seal onto the body of the device to prevent leaking of solution out of the device, even when the device is tilted so that solution contacts the interface of the lid and body. The lid allows the user to shake liquid and salts together to thoroughly mix the saline solution. The lid can optionally have an aperture that allows air to enter the device while solution is poured from the spout. The aperture can also allow a user to control the flow out of the spout, such as by covering the aperture. A small aperture in the lid allows the user to cover the aperture with a finger and prevent the liquid from leaking out of the device while shaking the solution. The body of the device can have contain eight ounces of liquid for forming a saline solution. Packets of saline are available for convenient mixing of eight ounces of saline solution.

The details of one or more implementations of the invention are set forth in the accompanying drawings and the description below. Other features, objects, and advantages of the invention will be apparent from the description and drawings, and from the claims.

DESCRIPTION OF DRAWINGS

FIGS. 1 and 2 are schematic side views of a device.

FIGS. 3A and 3B are schematic plan views of a lid and the device.

FIGS. 4 and 5 are schematic perspective views of devices with lids.

FIG. 6 is a flow chart for mixing a solution in the device.

FIG. 7 is a flow chart for using a device.

FIG. 8 is a schematic side view of a device with the lid on the device.

Like reference symbols in the various drawings indicate like elements.

DETAILED DESCRIPTION

Referring to FIG. 1, a nasal rinsing device 100 is shown. A body 10 forms a cavity that can hold liquid when the rinsing device 100 is in the upright position. The body 10 includes a spout 20 and a main portion 30. In some implementations, the main portion 30 has a bulbous shape. In one implementation, the main portion 30 has a substantially flat bottom 35 that allows the rinsing device 100 to remain upright when set on the bottom 35. Optionally, a handle 48 is positioned on the side of the main portion 30.

In one implementation, the spout 20 tapers from a wide portion 22 down to a narrow portion 24, where the wide portion 22 is closer to the main portion 30 of the body 10 than the narrow portion 24. At the end of the narrow portion 24 is a tip 40. The tip 40 is approximately conically shaped, with a convex curved surface leading from an end 42 of the tip 40 to the base 44 of the tip 40. In some implementations, the tip 40 is approximately gumdrop or mushroom cap shaped. An aperture in the end of the tip 40 allows liquid to flow from inside the main portion of the body 10 along the spout 20 and out the aperture. The aperture can be between 0.1 and 0.5 inches in diameter, such as about 0.25 inches or about 6.5 mm. In some embodiments, the body is about three inches tall.

The tip 40 includes a substantially smooth finish to allow a comfortable fit with a user's nostril. The tip 40 is sized to be comfortable for either a child or an adult. In some implementations, the tip 40 snugly fits within a nostril. In one implementation, the tip 40 has a length of about 0.6 inches or about 15 mm, a width at the base 44 of about 0.8 inches or 20 mm and a width at the end 42 of about 0.4 inches or 10 mm. The widest part, at the base 44, is sized to prevent the base 44 of the tip 40 from extending all the way into the user's nostril. The spout 20 forms an angle α of between about 30 and 60 degrees, such as about 45 degrees, with a plane parallel with the bottom 35 of main portion 30. In some implementations, the end 42 of the tip 40 is about parallel with the top of the body 10.

Referring to FIG. 2, in some implementations, the nasal rinsing device 100 includes a lid 50. The lid 50 is sized to snuggly fit onto the top of the body 10 and to form a liquid tight seal with the body 10. The lid 50 can have a cylindrical side wall 53. In some implementations of the device 100, the top of the exterior surface of the body 10 is threaded 60. The interior of the lid 50, such as inside the cylindrical side wall 53, can include mating threads so that the lid 50 can be screwed onto the body 10. In other implementations, the lid 50 snap fits onto the body 10. Other suitable means for mating the lid 50 to the body 10 can be used, such as a ring and groove assembly, a compression-fitting cap, exterior clamps or the like. In some implementations, the lid 50 is removable from the body 10 to allow the lid 50 to be removed and for liquid or solids to be added to the cavity in the body 10. In some implementations, the lid 50 has an apex portion 55. In some implementations, the lid 50 slopes upward from side of the cylindrical side wall 53 to a center of the lid 50.

Referring to FIG. 3A, a top view of lid 50 shows the apex of the lid 50. The lid 50 includes an aperture 65. In some implementations, the aperture 65 can have a diameter of between about 0.5 and 2 mm, such as about 1.5 mm. The aperture 65 is small enough for a user to cover the aperture with a finger and effectively plug the aperture 65.

Referring to FIG. 3B, a top view of the body 10 shows the aperture 63 for filling the body with fluid and salt. The aperture 66 in the end of the spout allows solution to be poured out of the body 10.

Optionally, the body 10 has a fill mark 62 to indicate how much solution is recommended for filling the body 10. The fill mark 62 can be a line drawn, embossed or otherwise indicated on the body 10. In some implementations, the fill mark 62 indicates about 8 ounces of water. The end 42 of the tip 40 is higher than the fill mark 62 to prevent liquid leaking out of the device when the device is in the upright position. In some embodiments, the fill line is about 1.5 inches below a top of device, which prevents spilling the from solution out of the device while maintaining a compact device size. In some embodiments, multiple fill marks are on the body 10, such as a fill mark at four ounces and a fill mark at eight ounces, so that the device can be used with different quantities of solution.

Referring to FIG. 4, a perspective view of the device 100 shows the device 100 in a closed configuration. When the device 100 is filled with liquid and the aperture 65 in the lid 50 is covered, liquid is prevented from flowing out of the aperture 66 in the tip 40 once the air pressure in the body 10 and the hydrostatic pressure of the solution are equal to the air pressure outside of the device 100. This is true even when the device 100 is tilted so that the aperture 66 in the tip 40 is below the liquid level in the body 100. Because the lid 50 is fit onto the body 10 with a liquid tight seal, the solution also does not leak out of the body 10 from between the lid 50 and the body 10.

Referring to FIG. 5, one implementation of a device 100 with a lid is shown. The spout 20 has a tapered length that lacks a gumdrop shaped tip. In some implementations, which are not shown, the body 10 lacks a bulbous portion, and is cylindrical, conical, oval, rectangular, or other suitable shape. An alternative embodiment of the device 100 with the lid is shown in FIG. 8.

The device 100 can be formed of a suitable rigid material, such as a resin, for example, polypropylene, another plastic material, glass, ceramic, copper, or stainless steel. In some implementations, the material is able to withstand the heat of lukewarm to hot water and is microwave safe to allow convenient heating of the contents in the device. In some embodiments, the body is formed of a different material from the spout or handle. In some embodiments, the spout and body are made in two separate pieces and welded, press fit or threaded to join the two pieces together. Further, the handle may be formed as a separate piece that is attached to the body by welding, fastening with mechanical fasteners or adhering, such as with an adhesive.

Referring to FIG. 6, a saline solution can be prepared treating a user with a device. The following steps can be performed in any order in addition to the order described. A mixture of sodium chloride (NaCl) and sodium bicarbonate (NaHCO$_3$) are added to the nasal lavage device (step 210). Packets containing a mixture of NaCl and NaHCO$_3$ for preparing a pH balanced, isotonic saline solution are available from NeilMed™ Products located in Santa Rosa, Calif. One size packet available contains an approximately 2.16 gram mixture of approximately 39 parts NaCl and 1 to 2 parts NaHCO$_3$, and can be used to prepare an isotonic saline solution having a concentration of approximately 0.9% to 1%, by dissolving the contents of the packet into 8 ounces of water (or 240 ml of water). A hypertonic saline solution can be prepared by dissolving two or three packets of the NaCl/NaHCO$_3$ mixture in 8 ounces of water. In some embodiments, a packet with 1.08 gram mixture of approximately 39 parts NaCl and 1 to 2 parts NaCl/NaHCO$_3$ can be mixed with 4 ounces of fluid to form 4 ounces of solution. In some embodiments, the device is configured to hold 16 ounces of solution.

The nasal lavage device is filled with water (step 220). Preferably distilled water is used, but purified, previously boiled water or clean tap water can also be used. The water is heated (step 230). The water can be heated to around body temperature. Alternatively, the water can be warmed before pouring it into the device or does not have to be warmed at all. The lid is placed on the lavage device to form a liquid tight seal (step 240). The user places his or her finger over the aperture in the lid, tilts the spout upwardly and shakes the device to dissolve the salt mixture in the water and form the saline solution (step 250).

Once the user has a nasal lavage device filled with saline solution, the user can use the saline as a treatment for nasal rinsing. Referring to FIG. 7, the user brings the nasal lavage device to a sink, holding his or her finger over the aperture to prevent the solution from spilling out of the device (step 310). The user then positions his or her body for lavage, standing in front of the sink (step 320). The user can bend slightly over the sink. Holding the device in the user's right hand, the user gently inserts the tip into the right nasal passage so that the tip snugly fits in the nasal passage. Keeping his or her mouth open, gradually tilts his or her head to the left and removes his or her finger from the aperture in the lid (step 330). The user allows the solution to flow into the nostril and drain out the other nostril of the nose (step 340). The user can control the flow of saline at any time by covering the aperture in the lid. The user then blows his or her nose gently, sniffing any residual solution in the nasal passage, e.g., once or twice, prior to blowing. Optionally, the user spits out any solution that might have dripped into his or her throat. The user repeats the process on the left side, holding the device in his or her left hand.

What is claimed is:

1. A device for nasal lavage, comprising:
   a body surrounding a cavity, the body having an upper portion, a side portion, and a bottom portion;
   a tubular portion with an interior space forming a conduit fluidly connected to the cavity in the body at the bottom portion, wherein the tubular portion extends from the bottom portion of the body to be substantially equivalent in height to the upper portion of the body and has an extended end, and wherein the tubular portion is configured at an angle of substantially 30°-60° relative to a base of the body;
   an end portion at the extended end of the tubular portion wherein the end portion has a bulbous tip to facilitate insertion of the end portion into a human nostril while disallowing the end portion from fully extending into the human nostril and wherein a termination of the end portion has a first aperture therethrough to enable fluid to flow from the cavity, through the conduit and out the first aperture;
   a handle attached to the body on an opposite side of the body as the tubular portion; and
   a lid configured to cover an opening in the upper portion of the body and to form a liquid tight seal with the body, the lid having a substantially cylindrical sidewall, a main surface and an apical portion with a second aperture therein, wherein the apical portion is located at a center of the main surface, and wherein the upper portion of the body is extended so as to ensure that the lid, when attached, is above a height of the first aperture in the end portion, and wherein:
      the second aperture in the lid is confined to a center of an upper surface of the apical portion of the lid, the upper surface being furthest from the cylindrical sidewall of the lid, the second aperture being sized and configured so as to be able to be sealed with a human finger and being of a second size that is less than the first size, the second aperture being in fluid communication with a passage that is in fluid communication with the cavity such that when sealed prohibits fluid from flowing out of the first aperture even when fluid maintained in the cavity exceeds a height of the first aperture,
   and
   wherein the body and lid are oriented such that when the body is placed on a surface, the termination of the end portion along with the opening in the upper portion of the body are at a first height relative to the surface while the apical portion with the second aperture is disposed at a second height that is greater than the first height above the surface.

2. The device of claim 1, wherein the first aperture in the end portion has a diameter that is less than a diameter of the conduit.

3. The device of claim 1, wherein the tubular portion tapers down from a widest portion adjacent to the body to the extended end.

4. The device of claim 1, wherein:
   the base includes a flattened portion configured to provide a stable resting surface for the body; and
   the tubular portion extends from the body at an angle between about 30° and 60° with a surface co-planar with the flattened portion.

5. The device of claim 4, wherein the body has a bulbous portion.

6. The device of claim 4, wherein the body includes a fill indication line.

7. The device of claim 1, wherein the lid is detachably secured to the body.

8. The device of claim 1, wherein an opening in the upper portion of the body has a diameter of at least about 2 inches.

9. The device of claim 1, wherein the cylindrical sidewall of the lid has a threaded inner diameter surface that is configured to mate with a cylindrical portion of the body having a threaded outer diameter surface.

10. The device of claim 1, wherein the bulbous tip is sized to fit snuggly against an interior of the human nostril.

11. The device of claim 10, wherein the end portion is about 0.7 inches in length.

12. The device of claim 1, wherein the end portion, the tubular portion, and the body are formed as a unitary piece.

13. The device of claim 1, wherein the body is formed of plastic.

14. The device of claim 1, wherein the first aperture in the end portion is about 0.25 inches in diameter.

15. The device of claim 1, wherein the apical portion is a protrusion that extends away from a center of a main portion of the lid.

16. The device of claim 1, wherein the aperture in the lid has a diameter between about 0.5 and 2mm.

17. A device for nasal lavage, comprising:
   a body surrounding a cavity, the body having an upper portion, a side portion, and a bottom portion;
   a tubular portion with an interior space fluidly connected to a bottom portion of the cavity in the body where the tubular portion extends from the bottom portion of the body and has an extended end opposite to the body, wherein the tubular portion is configured at an angle of substantially 30°-60° relative to a base of the body;
   an end portion at the extended end of the tubular portion, wherein a termination of the end portion includes a bulbous tip including a first aperture, wherein the first aperture is a first size;
   a handle attached to the body on an opposite side of the body as the tubular portion; and
   a lid configured to cover an opening in the upper portion of the body and to form a liquid tight seal with the body, the lid having a second aperture, the second aperture being sized and configured so as to be able to be sealed with a human finger and being of a second size that is less than the first size, wherein the second aperture being in fluid communication with a passage that is in fluid communication with the cavity such that when sealed prohibits fluid from flowing out of the first aperture even when fluid maintained in the cavity exceeds a height of the first aperture, wherein the lid includes an apical portion located at a center of a main surface, and wherein the upper portion of the body is extended so as to ensure that the lid, when attached, is substantially above a height of the first aperture in the end portion, wherein the body and lid are oriented such that when the body is placed on a surface, the termination of the end portion along with the opening in the upper portion of the body are at a first height relative to the surface while the apical portion with the second aperture is disposed at a second height that is greater than the first height above the surface.

\* \* \* \* \*